United States Patent
Wang et al.

(10) Patent No.: US 9,576,352 B2
(45) Date of Patent: Feb. 21, 2017

(54) METHOD TO DETERMINE SKIN-LAYER THICKNESS IN HIGH PRESSURE DIE CASTINGS

(71) Applicant: GM Global Technology Operations LLC, Detroit, MI (US)

(72) Inventors: Qigui Wang, Rochester Hills, MI (US); Wenying Yang, Rochester Hills, MI (US); James W. Knight, Davison, MI (US)

(73) Assignee: GM Global Technology Operations, LLC, Detroit, MI (US)

( * ) Notice: Subject to any disclaimer, the term of this patent is extended or adjusted under 35 U.S.C. 154(b) by 366 days.

(21) Appl. No.: 14/253,119

(22) Filed: Apr. 15, 2014

(65) Prior Publication Data
US 2015/0294448 A1 Oct. 15, 2015

(51) Int. Cl.
*G06T 7/00* (2006.01)
*G01N 21/88* (2006.01)

(52) U.S. Cl.
CPC ............ *G06T 7/0004* (2013.01); *G01N 21/88* (2013.01); *G06T 2207/30136* (2013.01)

(58) Field of Classification Search
None
See application file for complete search history.

(56) References Cited

U.S. PATENT DOCUMENTS

2012/0232685 A1* 9/2012 Wang .................. G06F 17/5018
700/98

OTHER PUBLICATIONS

Eutectic Systems, <http://academic.uprm.edu/pcaceres/Courses/MatEng/MSE7-2.pdf>.*
Weiler, J. P., J. T. Wood, R. J. Klassen, R. Berkmortel, and G. Wang. "Variability of skin thickness in an AM60B magnesium alloy die-casting." Materials Science and Engineering: A 419, No. 1 (2006): 297-305.*
Savvin, V. S., Yu A. Kazachkova, and Alexandr Alexandrovich Povzner. "Estimation of the temperature coefficient of surface tension of the interface between phases which form a eutectic." High Temperature 46, No. 2 (2008): 279-281.*
Otarawanna, S., C. M. Gourlay, H. I. Laukli, and A. K. Dahle. "The thickness of defect bands in high-pressure die castings." Materials Characterization 60, No. 12 (2009): 1432-1441.*

* cited by examiner

*Primary Examiner* — Sumati Lefkowitz
*Assistant Examiner* — Carol Wang (57) ABSTRACT

A quantitative metallographic method to measure skin layer thickness in high pressure die cast aluminum components. Because the faster-cooling skin layer region exhibits a higher volume fraction of eutectic phases than that of a slower-cooling inner region, measurements showing such higher eutectic phases can be used to quantify such layer thickness. An image at various thicknesses of a location of interest in a cast component sample is first obtained using an image analyzer, from which eutectic volume fractions within each of the received images may be determined. Comparisons of the determined volume fractions can be made against a known or predicted quantity for a particular alloy composition, and then correlated to the skin layer thickness via differences between the received or measured quantities and those of the known standard.

13 Claims, 9 Drawing Sheets

METHOD TO DETERMINE SKIN-LAYER THICKNESS IN HIGH PRESSURE DIE CASTINGS

BACKGROUND OF THE INVENTION

This invention is related generally to the quantification of properties in high pressure die cast (HPDC) aluminum alloys, and in particular to an improved quantitative metallographic methodology to accurately measure skin layer thickness in such cast components.

HPDC (also referred to as die casting) is being used extensively in the production of lightweight aluminum alloy components in general, and particularly for automotive components, such as engine blocks and transmission cases, as well as pistons or suspension parts. Low costs for large-scale production, close dimensional tolerances (near-net-shape) and smooth surface finishes are all positive attributes that make HPDC so attractive. Unlike alloys (such as 319 or 356) that are not typically used in HPDC, certain aluminum alloys, such as 380, 383, 390 or the like, are particularly well-suited to HPDC for their cost, strength, fluidity and generally good corrosion resistance qualities.

One disadvantage of the conventional HPDC process is that the parts are not amenable to heat treatment due to the presence of porosity in the casting that arises out of the dynamics peculiar to the HPDC process. As such, HPDC-produced aluminum parts are generally considered as having an outer skin region surrounding an inner region. In such structure, the region typically associated with the skin exhibits a relatively defect-free, dense microstructure, and has better mechanical properties than the region associated with the internal areas, where the voids, porosity and related defects are present. These defects are generally attributable to various factors one of which is shrinkage of the alloy from a low density liquid metal to a high density solid casting during solidification. Another contributing factor is the formation of gases, such as hydrogen or vapors from the decomposition of die wall lubricants, while still another factor is any entrapped air that occurs due to the rapidity with which the die is filled with the molten metal.

Thus, HPDC presents unique design challenges. Despite the location-specific nature of the mechanical properties mentioned above, conventional design approaches assume the presence of uniform microstructure and properties across the entirety of the cast component; much of this is due to the difficulty with which to accurately determine skin layer thickness. Such simplifying assumptions can in turn lead to unrealistic predictions of component structural properties through finite element analysis (FEA) or a related quantitative analysis tool. Inaccurate predictions may be particularly problematic in component failure analyses, as this can lead to either expensive warranty work or inefficient overdesign of the component; in either event, such inaccuracies impact the ability of the component designer to take full advantage of HPDC materials and processes.

SUMMARY OF THE INVENTION

The present inventors have determined that an accurate quantitative understanding of skin layer thickness is crucial to developing manufacturing processes that would lead to improved microstructures and related reliability in HPDC-produced aluminum alloy components. To that end, they have developed a new metallographic method to quantify local skin layer thickness in HPDC aluminum parts. In particular, the present inventors discovered that the volume fraction of eutectic phases in the skin layer region is higher than that in inner (i.e., core) regions due to the faster cooling (and reduced solute diffusion) rate in the solidified skin layer region relative to the remaining solidifying liquid of the inner region. This can be automatically measured and correlated to the thickness of the skin layer in an image analysis using a specially developed routine. In particular, the present inventors have recognized that the thickness of the skin layer is correlated to the distance from the casting free surface to the location where the volume fraction of eutectic phase changes from the higher value to that of a lower value based on the cooling and diffusion dynamics mentioned above. The approach identified herein would provide robust and quick means to determine more accurate property variations in HPDC cast components due to skin layer thickness. This in turn helps designers predict component performance and durability with a high degree of accuracy that leads to improved, more efficient product design with concomitant reductions in warranty costs.

According to a first aspect of the present invention, a method of determining skin layer thickness in an HPDC metal casting is disclosed. In particular, the present approach allows the accurate determination of the skin layer thickness through the measurement of the eutectic volume fraction. The method includes receiving an image (or multiple images) of a location of interest in a metal casting sample or specimen. In one form, the image comprises a large mosaic of various fields that make up the specimen as a way to subdivide the received image into smaller geometric grid shapes that can more easily quantify eutectic and non-eutectic portions of the scanned image. Once the image of the sample being analyzed has been received, the volume fraction of eutectic is determined. This volume fraction is then correlated to the skin layer thickness through predetermined (i.e., known) quantities of a known alloy (such as 380 or the like) being used in the HPDC metal casting.

In one particular form, the predicted quantity is made up of particular locations on a phase diagram (such as a binary phase diagram) of the known alloy. Likewise, the receiving of the images can be performed by an image analysis system, while the determination of a eutectic volume fraction is preferably done by quantifying contrasting light and dark portions of the received images at each depth layer within the location of interest in the component. Algorithms (which can in one form be performed by a processor or related computation device) performs the comparisons of the idealized alloy and the received images using various points of confluence between the solidus, solvus and eutectic isotherm lines, as well known initial liquid alloy concentrations of the primary alloy constituents (such as aluminum and silicon in the case of 380 and other HPDC-compatible alloys). In this way, an accurate determination of where the outer region (which corresponds to the skin layer thickness) ends and the inner region (which corresponds to a layer contained within the skin layer thickness) begins can be known based on differences between the predicted and measured values.

In another particular form, the method includes configuring a computerized system to receive numerous images corresponding to varying depths of a location of interest in a sample of the component. From this, a eutectic volume fraction within each of the received images can be determined by quantifying contrasting portions on the images, after which the determined volume fraction is compared against a predicted phase diagram quantity of the known alloy. In this way, differences between the predicted quantity and the determined volume fraction are used to correlate the skin layer thickness.

According to another aspect of the present invention, a method of determining skin layer thickness in an HPDC component includes configuring an image analysis system to receive images corresponding to varying depths of a location of interest in a sample of the component. From this, a eutectic volume fraction within each of the received images is determined by quantifying contrasting portions and comparing the determined volume fraction against a predicted phase diagram quantity of a known alloy that is being used in the component. As before, differences between the predicted quantity and the determined volume fraction are correlated to the skin layer thickness.

According to yet another aspect of the present invention, an article of manufacture including a computer usable medium having computer readable program code embodied therein for determining skin layer thickness in a high pressure die cast component is disclosed.

BRIEF DESCRIPTION OF THE DRAWINGS

The following detailed description of the preferred embodiments of the present invention can be best understood when read in conjunction with the following drawings, where like structure is indicated with like reference numerals and in which:

FIGS. 5A and 5B show examples of metallographic images of the first of the areas of the transmission case of FIG. 4, including measurement results of eutectic phases and porosity where FIG. 5A is for a microstructure image of the area and the actual location measured and FIG. 5B is a graph for the measured area fraction of the eutectic phase across the wall thickness in the area;

FIGS. 6A and 6B show examples of metallographic images of the second of the areas of the transmission case of FIG. 4, including measurement results of eutectic phases and porosity where FIG. 6A is for a microstructure image of the area and the actual location measured and FIG. 6B is a graph for the measured area fraction of the eutectic phase across the wall thickness in the area;

FIGS. 7A and 7B show examples of metallographic images of the second of the areas of the transmission case of FIG. 4, including measurement results of eutectic phases and porosity where FIG. 7A is for a microstructure image of the area and the actual location measured and FIG. 7B is a graph for the measured area fraction of the eutectic phase across the wall thickness in the area;

FIGS. 8A and 8B show examples of metallographic images of the second of the areas of the transmission case of FIG. 4, including measurement results of eutectic phases and porosity where FIG. 8A is for a microstructure image of the area and the actual location measured and FIG. 8B is a graph for the measured area fraction of the eutectic phase across the wall thickness in the area;

FIGS. 9A and 9B show examples of metallographic images of the second of the areas of the transmission case of FIG. 4, including measurement results of eutectic phases and porosity where FIG. 9A is for a microstructure image of the area and the actual location measured and FIG. 9B is a graph for the measured area fraction of the eutectic phase across the wall thickness in the area; and FIGS. 10A and 10B show examples of metallographic images of the second of the areas of the transmission case of FIG. 4, including measurement results of eutectic phases and porosity where FIG. 10A is for a microstructure image of the area and the actual location measured and FIG. 10B is a graph for the measured area fraction of the eutectic phase across the wall thickness in the area.

DETAILED DESCRIPTION OF THE PREFERRED EMBODIMENTS

Figure 1:
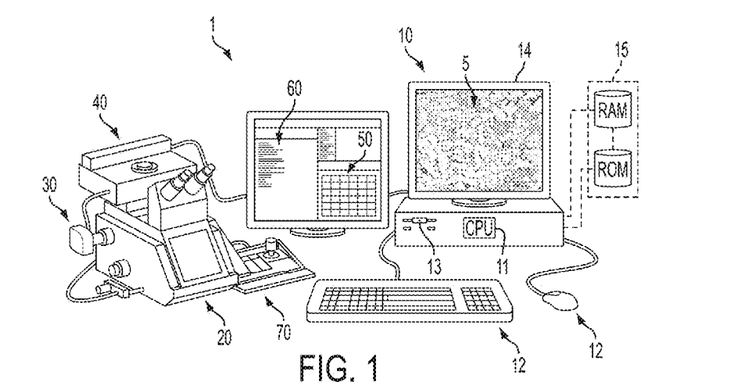
FIG. 1 shows a computerized system that can be used to measure and quantify skin layer thickness according to an aspect of the present invention.

Referring first to FIG. 1, an automated way to measure eutectic phases may be performed on a digital computer or related electronic device configured as an image analysis (IA) system 1; such a system may also be referred to as an image analyzer system, image analyzer or the like. In situations where system 1 is computer-based in the manner discussed below (as well as suitable variants thereof), it is referred to as having a von Neumann architecture. Likewise, a particularly-adapted computer or computer-related data processing device that employs the salient features of such an architecture in order to perform at least some of the data acquisition, manipulation or related computational functions, is deemed to be compatible with the method of the present invention. It will be appreciated by those skilled in the art that computer-executable instructions that embody the calculations discussed elsewhere in this disclosure can be made to achieve the objectives set forth in the present invention.

System 1 includes a computer 10 or related data processing equipment that includes a processing unit 11 (which may be in the form of one or more microprocessors or related processing means), one or more mechanisms for information input 12 (including a keyboard, mouse or other device, such as a voice-recognition receiver (not shown)), as well as a one or more loaders 13 (which may be in the form of magnetic or optical memory or related storage in the form of CDs, DVDs, USB port or the like), one or more display screens or related information output 14, a memory 15 and computer-readable program code means (not shown) to process at least a portion of the received information relating to the aluminum alloy. As will be appreciated by those skilled in the art, memory 15 may be in the form of random-access memory (RAM, also called mass memory, which can be used for the temporary storage of data) and instruction-storing memory in the form of read-only memory (ROM). In addition to other forms of input not shown (such as through an internet or related connection to an outside source of data), the loaders 13 may serve as a way to load data or program instructions from one computer-usable medium (such as flash drives or the aforementioned CDs, DVDs or related media) to another (such as memory 15). As will be appreciated by those skilled in the art, computer 10 may exist as an autonomous (i.e., stand-alone) unit, or may be the part of a larger network such as those encountered in cloud computing, where various computation, software, data access and storage services may reside in disparate physical locations. Such a dissociation of the computational resources does not detract from such a system being categorized as a computer.

In a particular form, the computer-readable program code that contains the algorithms and formulae mentioned above can be loaded into ROM that is part of memory 15. Such computer-readable program code may also be formed as part of an article of manufacture such that the instructions contained in the code are situated on a magnetically-readable or optically-readable disk or other related non-transitory, machine-readable medium, such as flash memory device, CDs, DVDs, EEPROMs, floppy disks or other such medium capable of storing machine-executable instructions and data structures. Such a medium is capable of being accessed by computer 10 or other electronic device having processing unit 11 used for interpreting instructions from the computer-readable program code. Together, the processor 11 and any program code configured to be executed by the processor 11 define a means to perform one or more of the pore size and distribution calculations discussed herein. As will be understood by those skilled in the computer art, a computer 10 that forms a part of image analysis system 1 may additionally include additional chipsets, as well as a bus and related wiring for conveying data and related information between processing unit 11 and other devices (such as the aforementioned input, output and memory devices). Upon having the program code means loaded into ROM, the computer 10 of system 1 becomes a specific-purpose machine configured to determine HPDC component skin layer thickness properties in a manner as described herein. In another aspect, system 1 may be just the instruction code (including that of the various program modules (not shown)), while in still another aspect, system 1 may include both the instruction code and a computer-readable medium such as mentioned above.

It will also be appreciated by those skilled in the art that there are other ways to receive data and related information besides the manual input approach depicted in input 12 (especially in situations where large amounts of data are being input), and that any conventional means for providing such data in order to allow processing unit 11 to operate on it is within the scope of the present invention. As such, input 12 may also be in the form of high-throughput data line (including the internet connection mentioned above) in order to accept large amounts of code, input data or other information into memory 15. The information output 14 is configured to convey information relating to the desired casting approach to a user (when, for example, the information output 14 is in the form of a screen as shown) or to another program or model. It will likewise be appreciated by those skilled in the art that the features associated with the input 12 and output 14 may be combined into a single functional unit such as a graphical user interface (GUI).

Figure 2A:
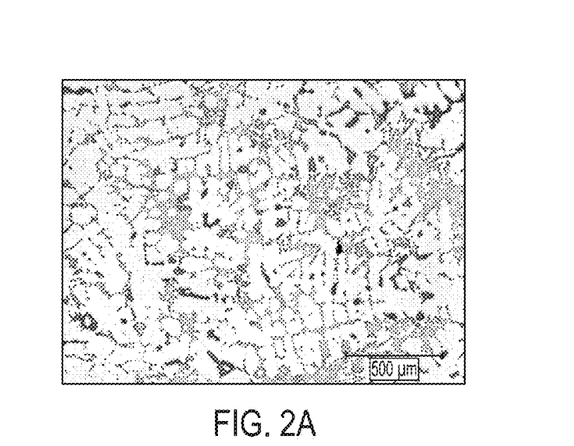
FIG. 2A shows a cutaway surface from a notional cast aluminum alloy.
Figure 2B:
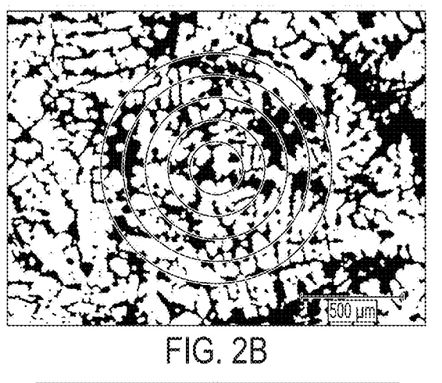
FIG. 2B shows a metallographic representation of the casting of FIG. 2A with an overlaid grid.

Referring next to FIGS. 2A and 2B in conjunction with FIG. 1, IA system 1 is used to extract information from images 5, in particular, using metallographic techniques to acquire eutectic properties of the casting sample or specimen of interest. Starting with a prepared (for example, polished) metallographic sample, a microscope 20 or related scanner or visual acquisition device is used to magnify and display on output 14 the image 5 that is captured by the camera 30. Typically, many images 5 are captured through the use of a motorized stage 40 and stage pattern 50. A stage controller 70 (which employs joy stick-like control) may be used to move the micrograph of the material sample from one field to another field in the microscope 20 through a two or three-dimensional (Cartesian) series of x, y and z (focus) stage movements. This allows movement across a stage pattern 50 to permit analyzing multiple fields of view over the sample. This automated stage pattern 50—which includes auto focus features—permits the capture of large amounts of data in a short period of time. The joy stick of stage controller 70 allows movement of the stage while observing the sample through the eyepiece of microscope 20 to facilitate the selection of particular areas upon which the analysis of the present invention will be performed.

Figure 2C:
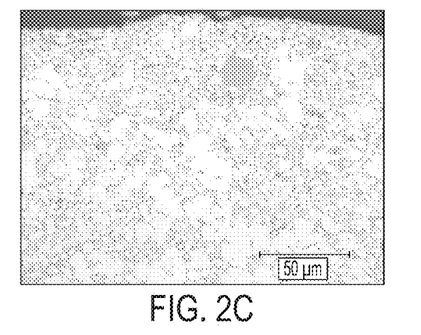
FIG. 2C shows a microstructure of a notional skin layer region of an HPDC produced component using 380 alloy.
Figure 2D:
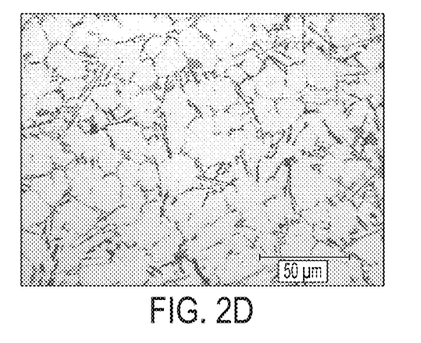
FIG. 2D shows a microstructure of a notional center core region of an HPDC produced component using 380 alloy.

Initially, a microstructure of a representative aluminum casting as shown in FIG. 2A is optically captured or otherwise received by IA system 1 as a micrograph. In a particular form, the micrograph can be viewed, stored and analyzed as a mosaic image made up of smaller subdivided portions. The digital image of the microstructure is dilated and then eroded one or more times in IA system 1 to better enhance the eutectic region, such as by making it appear completely filled via the darkened-in region in FIG. 2B. The area fraction of the dark region is measured by IA system 1. While dark and light (for example, black and white) imaging is preferable, gray thresholding may optionally be performed on these digitized images 5 in a computer-based routine or algorithm 60 (shown in user-readable form on a display) that make up the image analysis software stored in memory 15 or other suitable computer-readable medium. In such case, the IA system 1 uses the gray level thresholds and divides the level between black and white into many power of 2 intervals (such as between 0 and 256 for 8 bit data formats). In a preferred form, the alternating dark and light portions of the received image are automatically identified by optical microscope 20 (or related mechanized device) based on the gray level contrast between the eutectic and non-eutectic portions. The IA system 1 will then accept these identified portions and measure them automatically. FIGS. 2C and 2D show representative skin (FIG. 2C) and inner (FIG. 2D) regions of a notional HPDC sample of A380 alloy used to prepare a transmission case.

Figure 3:
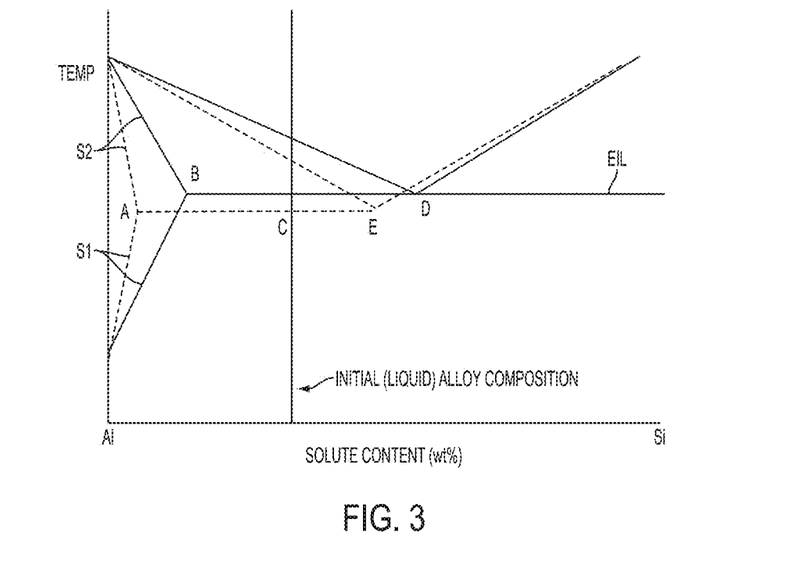
FIG. 3 shows a representative Al—Si phase diagram under conditions of equilibrium (solid lines) and non-equilibrium (dashed lines)

Next, the relationship between the cooling rate and the volume fraction of eutectic phases is determined. FIG. 3 schematically shows the effect of cooling rate on solidification process from the phase diagram point of view. In the equilibrium solidification condition (i.e., the inner region of the casting, where very slow solidification takes place), the change of phase transformation and alloy compositions in both liquid and solid follows the solid lines in the figure, while in the fast cooling condition (i.e., the outer or skin layer region of the casting), the solute concentration in both solid and liquid phases alters along the figure's dashed lines. As mentioned above, the volume fraction of eutectic phases is increased in the fast solidified microstructure for any given initial alloy composition. In the example shown, an aluminum-silicon binary alloy has a silicon solute concentration C in an aluminum solvent. The location A represents the intersection of the solvus line S1, solidus line S2 of aluminum matrix and eutectic isotherm line EIL for the maximum Si solubility (or max Si content) in the aluminum matrix of an outer region of the alloy, location B represents the intersection of the solvus line S1, solidus line S2 of aluminum matrix and eutectic isotherm line EIL for the maximum Si solubility (or max Si content) in the aluminum matrix of an inner region of the alloy, location D represents a eutectic point of an inner layer region and location E corresponds to the eutectic point of an outer layer region.

Thus, the difficulties in using a single plot (for example, the slow solidification eutectic line B-D) to calculate theoretical eutectic volume fraction (as well as eutectic volume fraction differences between the skin layer and the core) with very fast cooling prompted the present inventors to move the eutectic line B-D down to the location represented by the A-E line; this movement (represented by the equations below) reconciles theoretical eutectic volume fraction predictions with observed experimental results.

In the equilibrium (very slow) solidification condition that corresponds to the inner (i.e., core) region of the casting, the volume fraction of eutectic can be estimated by:

$$\text{Vol \% Eutectic}_{inner\ region} = (C_{w/o} - B_{w/o})/(D_{w/o} - B_{w/o})$$

or:

$$\text{Vol \% Eutectic}_{inner\ region} = BC/BD$$

Likewise, under the condition of fast cooling that corresponds to the outer (i.e., skin layer) region of the casting, the volume fraction of the eutectic can also be estimated from the phase diagram using the dashed lines:

$$\text{Vol \% Eutectic}_{outer\ region} = (C_{w/o} - A_{w/o})/(E_{w/o} - A_{w/o})$$

or:

$$\text{Vol \% Eutectic}_{outer\ region} = AC/AE$$

In particular, the equations above provide a qualitative estimate for an Al—Si binary phase diagram. Thus, keeping in mind that an actual alloy (such as 380 or the like) further includes multiple alloying elements, using computational thermodynamic software to calculate the microstructures solidified at very fast cooling rate may be difficult or prohibitively costly. Instead, the estimates above take advantage of the fact that the solid lines in the phase diagram are known, and from this a baseline (such as for the Al—Si binary alloy) can be established. The dashed lines—which correspond to points A and E in the figure and are not well established in the known art—are made (through the equations above) to relate to the actual cooling rate of the components in question. As the concentration of weight percent of A (i.e., $A_{w/o}$) under the faster cooling conditions is less than that of the slower cooling conditions of B, the volume percent of eutectic in the fast cooled skin layer is larger than that of the slowly solidified central core regions. As described next, the above equations may be used to correlate such volume fraction of eutectic to the different outer and inner regions.

Figure 4:
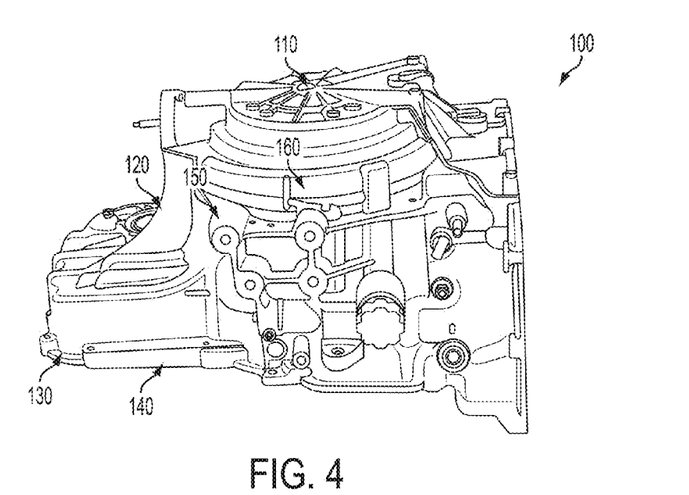
FIG. 4 shows a notional HPDC aluminum alloy automotive transmission case with six different locations of various sample sites.

Samples were taken from six different locations of the transmission case 100 of FIG. 4; the area percentage of eutectic was determined by an image analysis routine embodied on IA system 1 over a various number of fields of view at 200× magnification. The area percentage of eutectic includes eutectic particles and eutectic aluminum between the particles, while the aluminum matrix is not uniform, with many alpha aluminum dendrites present. The eutectic silicon particles (dark gray script and blades) are fully unmodified at the center of the sections and modified at the surfaces. In general, these unmodified silicon particles are large and elongated, leading to low ductility and fracture toughness of the material. The degree of modification correlates to the area percentage of eutectic present.

The first field of view was at the cast surface of the area to a depth of 0.396 mm (the depth of one field of view). The analysis continued in increments of 0.396 mm to the opposite wall. Areas 110, 120, 130, and 150 have a cast surface on both sides while areas 140 and 160 have a cast surface at the first field of view and a machined surface at the last field of view. Each field of view is approximately 0.525 mm times 0.396 mm for an area of 0.208 mm². The image analyzer has a resolution at 200 times (i.e., 200×) magnification of 0.326797 µm/pixel, and a measurement uncertainty (i.e., the uncertainty associated with the stage micrometer and the uncertainty associated with the resolution) is ±0.6430 µm.

The area percentage of porosity was determined by image analysis routine over the recorded number of fields of view at 200× magnification. The smallest size used for the area percent is 10 µm². The area percentage of eutectic analysis was performed across the wall thickness in each area, and mosaic images of the micro sections are shown in FIGS. 5A, 6A, 7A, 8A, 9A and 10A. The measured area percentages of eutectic in the corresponding samples are shown in FIGS. 5B, 6B, 7B, 8B, 9B and 10B. Respective measured area percentages of porosity in the samples (not shown) may also be included to provide evidence of high porosity in the inner (core) area.

Figure 5A:
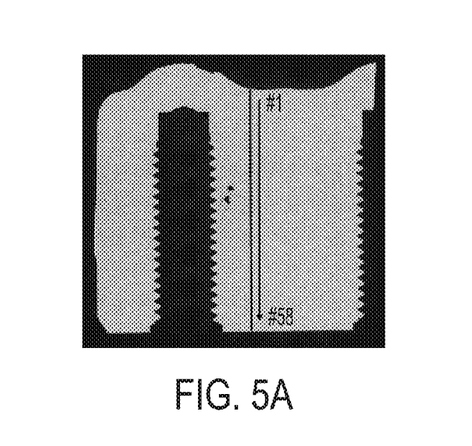
Figure 5B:
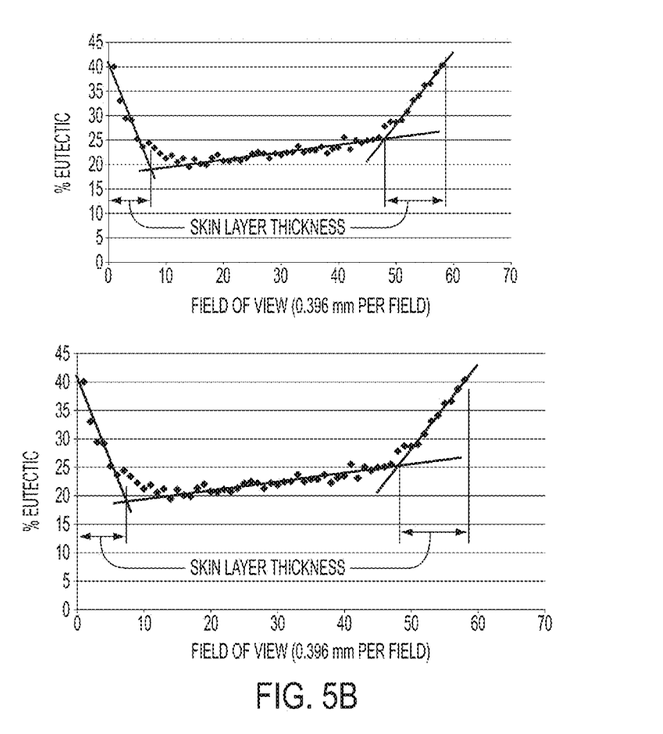
Figure 6A:
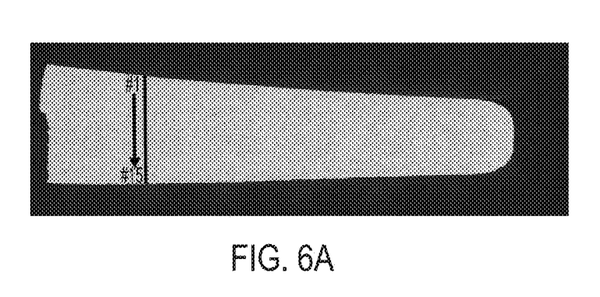
Figure 6B:
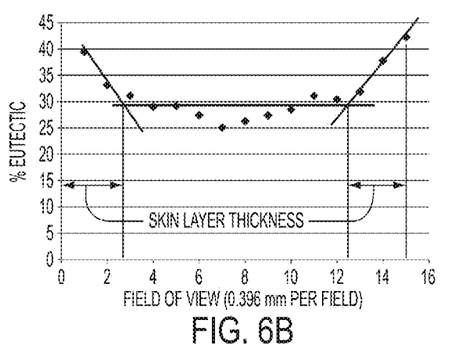
Figure 7A:
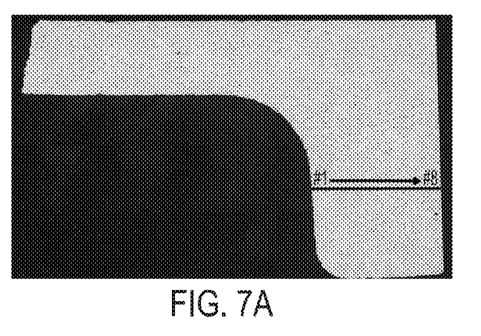
Figure 7B:
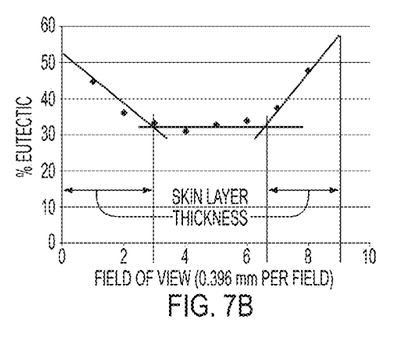
Figure 8A:
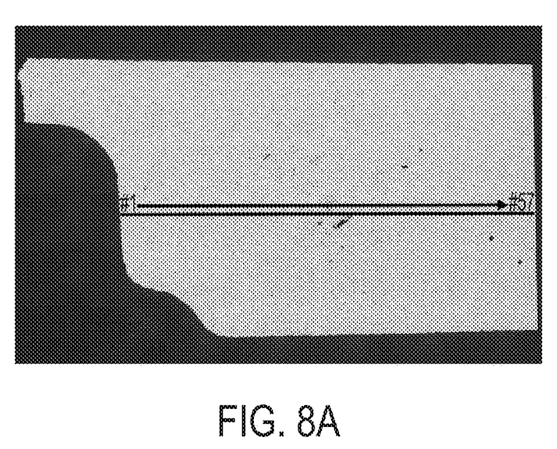
Figure 8B:
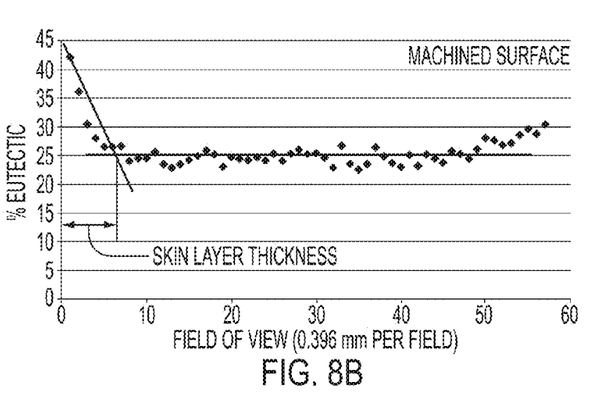
Figure 9A:
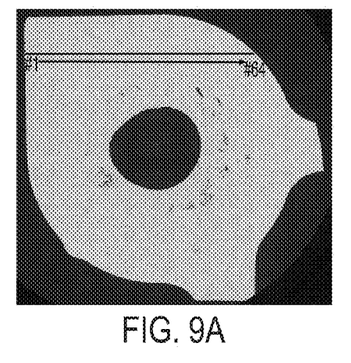
Figure 9B:
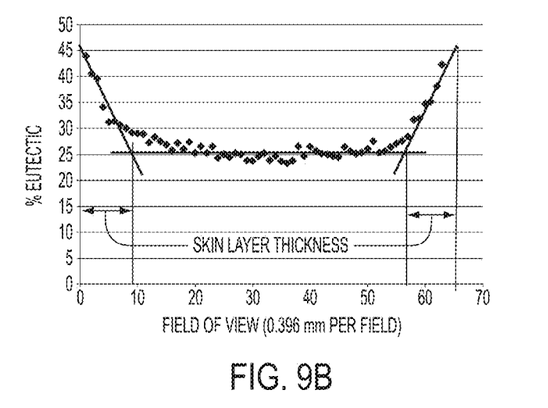
Figure 10A:
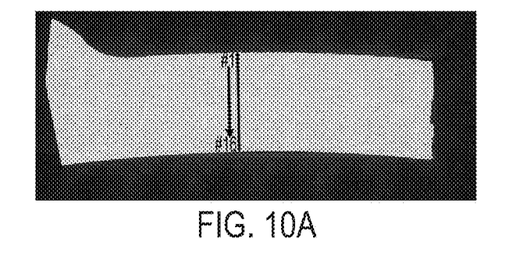
Figure 10B:
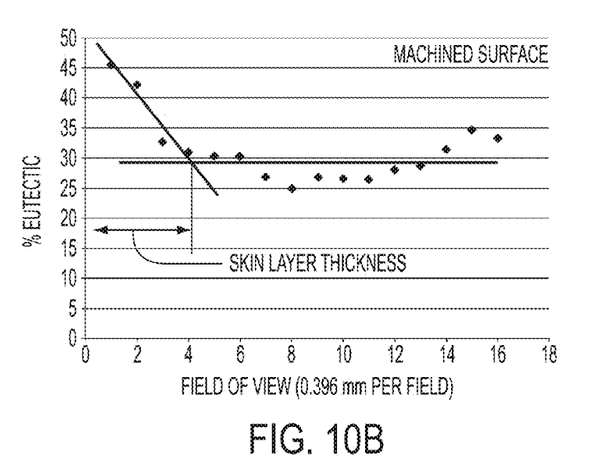

Referring with particularity to FIGS. 5A and 5B, measurement results of eutectic phases and porosity taken at fifty eight different fields of view depths are shown. In particular, FIG. 5A shows a microstructure image of area 110 and the actual location measured, while FIG. 5B shows a mapping of the percentage of eutectic phase at each of the fifty eight sample points that correspond to the wall thickness depths. Based on the measurements shown in FIG. 5B, it can be seen that the skin layer thickness for that particular location in the tranmission case is between 8 to 10 field depths (which is the equivalent of between 3 and 4 mm). Similar results can be seen for the remaining sample sites of FIGS. 6A through 10B, where (for example) FIGS. 6A and 6B show that the skin layer thickness for that particular location in the tranmission case is between 2 to 3 field depths (which is the equivalent of between 0.8 and 1.2 mm).

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. Moreover, the term "substantially" is utilized herein to represent the inherent degree of uncertainty that may be attributed to any quantitative comparison, value, measurement, or other representation. As such, it may represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of determining skin layer thickness in a high pressure die cast component, said method comprising:

providing an image analysis system having a computer, a memory, and a camera;

receiving a plurality of images from said camera corresponding to varying depths of a location of interest in a sample of said component;

determining a eutectic volume fraction within each of said plurality of received images;

comparing said determined volume fraction against a predicted quantity; and correlating differences in said comparison to said skin layer thickness.

2. The method of claim 1, wherein said predicted quantity comprises particular locations on a phase diagram of a known alloy used in said component.

3. The method of claim 2, wherein determining a eutectic volume fraction within each of said plurality of received images further comprises determining a eutectic volume fraction within each of said plurality of received images using quantifying contrasting light and dark portions of a respective one of said received images.

4. The method of claim 3, wherein providing an image analysis system having a computer, a memory, and a camera further comprises providing an image analysis system having a computer, a memory, and a camera, and wherein said memory includes at least one algorithm for performing said comparing.

5. The method of claim 4, wherein said determining a eutectic volume fraction is performed by said algorithm through the following calculations:

Vol % EutectiCinnerregion=$BC/BD$

Vol % EutectiCouterregion=$AC/AE$ where A represents a location on said phase diagram that corresponds to the intersection of the solvus line, solidus line and eutectic isotherm line for an outer region of the alloy used in said component, B represents a location on said phase diagram that corresponds to the intersection of the solvus line, solidus line and eutectic isotherm line for an inner layer region of the alloy used in said component, C represents an initial liquid alloy concentration of aluminum or silicon of the alloy used in said component, D represents a location on said phase diagram that corresponds to the eutectic point of an inner layer region of the alloy used in said component and E corresponds to the eutectic point of an outer layer region of the alloy used in said component.

6. The method of claim 5, wherein said outer region corresponds to said skin layer thickness and said inner region corresponds to a layer contained within said skin layer thickness.

7. A method of determining skin layer thickness in a high pressure die cast component, said method comprising:

configuring an image analysis system to receive and store a plurality of images, each of the plurality of images corresponding to varying depths of a location of interest in a sample of said component;

determining a eutectic volume fraction within each of said plurality of images by quantifying contrasting light and dark portions; and comparing said determined volume fraction against a predicted phase diagram quantity of a known alloy used in said component, wherein differences between said predicted quantity and said determined volume fraction are used to correlate said skin layer thickness.

8. The method of claim 7, wherein said determining a eutectic volume fraction is performed by said algorithm using the following calculations:

Vol % EutectiCinnerregion=$BC/BD$

Vol % EutectiCouterregion=$AC/AE$ where A represents a location on said phase diagram that corresponds to the intersection of the solvus line, solidus line and eutectic isotherm line for an outer region of the alloy used in said component, B represents a location on said phase diagram that corresponds to the intersection of the solvus line, solidus line and eutectic isotherm line for an inner layer region of the alloy used in said component, C represents an initial liquid alloy concentration of aluminum or silicon of the alloy used in said component, D represents a location on said phase diagram that corresponds to the eutectic point of an inner layer region of the alloy used in said component and E corresponds to the eutectic point of an outer layer region of the alloy used in said component.

9. An article of manufacture comprising a computer memory having computer readable program code embodied therein for determining skin layer thickness in a high pressure die cast component, said computer readable program code in said article of manufacture comprising:

computer readable program code portion for causing a computer to accept data pertaining to digital information of a location of interest within a sample of said high pressure die cast component;

computer readable program code portion for causing said computer to process said digital information into a eutectic volume fraction;

computer readable program code portion for causing said computer to convert said eutectic volume fraction into a corresponding skin layer thickness through an algorithm based on at least one of an empirical relationship and a theoretical relationship; and computer readable program code portion for causing said computer to produce an output that corresponds to said skin layer thickness.

10. The article of manufacture of claim 9, wherein said computer readable program code portion for causing said computer to convert said eutectic volume fraction into a corresponding skin layer thickness through an algorithm based on at least one of an empirical relationship and a theoretical relationship is performed by said algorithm using the following calculations:

Vol % EutectiCinnerregion=$BC/BD$

Vol % EutectiCouterregion=$AC/AE$ where A represents a location on said phase diagram that corresponds to the intersection of the solvus line, solidus line and eutectic isotherm line for an outer region of the alloy used in said component, B represents a location on said phase diagram that corresponds to the intersection of the solvus line, solidus line and eutectic isotherm line for an inner layer region of the alloy used in said component, C represents an initial liquid alloy concentration of aluminum or silicon of the alloy used in said component, D represents a location on said phase diagram that corresponds to the eutectic point of an inner layer region of the alloy used in said component and E corresponds to the eutectic point of an outer layer region of the alloy used in said component.

11. The article of manufacture of claim 9, wherein said computer memory is selected from the group consisting of random-access memory and read-only memory.

12. The article of manufacture of claim 9, wherein said computer memory is configured as a computer input device.

13. The article of manufacture of claim 12, wherein said computer input device is selected from the group consisting of flash drives, compact disks and digital video disks.

* * * * *